(12) United States Patent
Wyss

(10) Patent No.: US 6,227,210 B1
(45) Date of Patent: May 8, 2001

(54) DISPOSABLE X-SHAPED FLOSSER

(76) Inventor: John Raymond Wyss, 9020 Greenwood Ave. N., Seattle, WA (US) 98103

( * ) Notice: Subject to any disclaimer, the term of this patent is extended or adjusted under 35 U.S.C. 154(b) by 0 days.

(21) Appl. No.: 09/507,636

(22) Filed: Feb. 22, 2000

(51) Int. Cl.⁷ .................................................. A61C 15/00
(52) U.S. Cl. .......................................................... 132/323
(58) Field of Search ................................... 132/323, 324, 132/325, 326, 327

(56) References Cited

U.S. PATENT DOCUMENTS 4,006,750 * 2/1977 Choderow ............................ 132/323
5,123,432 * 6/1992 Wyss ..................................... 132/323
5,433,227 * 7/1995 Chen ..................................... 132/323

* cited by examiner

Primary Examiner—Nicholas D. Lucchesi

(57) ABSTRACT

A flosser having a framework and a length of floss incorporated therein is disclosed. The framework has a configuration which allows for exposed portions of floss at opposite ends of the framework. A flosser mold is also disclosed which allows for manufacture of the flosser using conventional plastic injection molding techniques. The mold comprises a plurality of receptacles and pins which allow for precise capture and positioning of a strand of floss during the injection molding process.

2 Claims, 1 Drawing Sheet

DISPOSABLE X-SHAPED FLOSSER

BACKGROUND OF THE INVENTION

Figure 1:
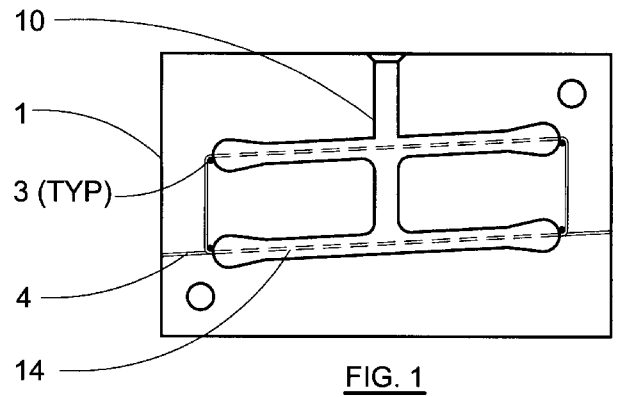

The prior art is varied and extensive for both disposable and non-disposable flossing tools and dental floss holders. Henne, Chodorow, and Johnson all patented a type of dental floss holding tool for easing the important job of flossing teeth. None provided the level of durability needed for complete dental flossing to the levels required for true hygiene and periodontal maintenance. My own U.S. Pat. No. 5,123,432, Jun. 23, 1992, advanced the design by providing a high degree of structural integration of a floss loop into a plastic frame, the combination being disposable after use. Leverage action is provided so that the working lengths of floss could be held taught and easily inserted between teeth at very tight points of interdental contact. The fundamental advantages of that tool have distinct superiority over other disposable designs because the integration of a loop of floss and a plastic frame provide optimum strength. Utility, efficiency and ease of use is excellent in that tool, results of its featured leverage action. The problem found in prototyping and testing that flossing tool was difficulty of manufacture, since floss loops are not commonly manufactured. Holding a floss loop within a plastic injection mold is a difficult procedure due to the extreme pressures exerted within the mold cavities which tend to move the floss aside as cavities are displaced with molten plastic. The X-shaped tool provides an improved narrower design, since the width of the H-shaped tool restricted reach to the rear teeth. The X-shaped flosser is easily manufactured with a modified thermal plastic injection mold, and uses floss from a spool source, not solid loops. These improvements make the new tool inexpensive and easy to manufacture. At the same time the new tool itself provides the maximum structural integrity and provides leverage action in a disposable tool, designed for comfort and ease in reaching between very difficult to floss rear teeth. Additional tool strength is gained due to its construction method wherein an integral strand of floss runs the entire length of the frame members of the tool. This construction supports the floss while tensioned and under high stress factors which are common while normal flossing of teeth is performed.

SUMMARY

An H-shaped rib centrally located within the X-shaped framework reinforces and provides positive fulcrum action in the tool. Integration with the corresponding working lengths of said floss at the ends of the tool are made by improving the integral combination of the plastic frame and floss. More durability and utility in the working lengths of the floss are provided by protecting against separation of the floss from the tool while in use and under stress. In the present invention, this is accomplished with simple modifications to existing thermal plastic injection type molds whereby capture points are provided to accept and secure floss which is dispensed from a typical floss spool source.

The purpose of this invention is to provide a highly durable, low cost disposable flossing tool featuring leverage action. An object is to utilize a typical thermal plastic injection mold, consisting of two mold halves with cavity areas which fill with liquid plastic to form a floss holding framework, fitted with capture points in the form of pins, perpendicular to the inner mold half surfaces. Thereby the floss may be routed from its spool source and through the cavities of the mold about the pins, which provides floss capture points when said halves are closed together and ready for injection. Upon injection of liquid heated plastic, the floss tends to remain in its various pre-established position since it is secured at the capture points and around the pins within the mold. By virtue of this method of positively holding the floss within a thermal injection mold, the entire frame of an X-shaped tool can be embedded with said floss, providing an ultradurable disposable dental flosser. It is an objective to retain the advantages of the H-shaped tool of U.S. Pat. No. 5,123,432 and improve the tool by using the newly designed X-shaped framework.

Additional objectives are to provide single hand operation of leverage action, keeping the floss taut while working with tight teeth, to provide a narrow profile allowing a user to easily access rear teeth, and to provide double ended capability, convenience and disposability in a low cost tool that is easily used by anyone, young or old, without extraordinary skill or strength.

The X-shaped flossing tool is a cleaner, more effective and easier method for most users than other methods of flossing. Softer tools, using butyl or rubber in the frame, can be used for children or elderly with sensitive gums, and various types of floss and flavorings can be adapted for personal preferences. Through application of a number of typical leverage designs and devices employing wobble-type mechanisms, or in a tendon-like fashion, the flossers can demonstrate a flexible hinge-like movement with angular variation at its center, in a bending motion, allowing an angular approach to the rear teeth.

PREFERRED EMBODIMENT OF THE INVENTION

The preferred embodiment of the invention shown herein is a result of extensive testing and prototyping and is constructed of an X-shaped injection molded rigid non-toxic plastic framework with floss made of standard nylon, superstrong polyester and/or polytetrofluroethylene (a slippery non-shredding floss), excellent for use where prior dental work is present which would put additional wear and tear on floss. A denier of 1,200–1,500 for the fiber has been suitable, however individuals may wish to specify their own floss thickness. Capture points provided are pins within mold halves, and floss is installed prior to injection, and held in place upon said pins until closed between the mold halves, wherein the typical clamping pressure of thermal plastic injection molding equipment is adequate to hold the floss in place.

DESCRIPTION OF THE INVENTION

FIG. 1: INNER FACE OF MOLD SHOWING CAPTURE POINTS AND LOADED FLOSS

FIG. 2: MOLD HALVES OPENED SHOWING INJECTION RESULTS

FIG. 3: X-SHAPED FLOSSING TOOL SHOWING TRIMMED APPEARANCE

FIG. 1: Turn now your attention to FIG. 1. Shown is an inner face of a typical injection mold base which will manufacture the H-shaped flossing tool as described herein. This frontal view faces one half (1) of the injection mold of the dental floss holding device. Upright capturing pins (3) are set into the mold face perpendicularly at four remote corners of the mold cavity (10). Floss (4) from a spool is laid within the mold, entering at one side and routed through said mold cavity. Material introduced into the mold cavity will envelope and thereby integrate with floss in the cavity area, where said floss is held in place by said capturing pins. The integrated portions of floss are indicated here by the floss within the cavity area drawn in broken lines (14). Said floss is wound onto the four capturing pins, and routed into a rectangular loop, double thickness in its second path through the cavity wherein floss made its entry, and exits the mold at the side opposing the entry. Winding and routing the floss in this manner allows for use of bulk floss from a spool for greatest economy. Winding several adjacent cavities for injection at the same time is possible using one length of floss, which creates economically feasible mass production opportunities using multiple cavities in a single mold, a technique widely used in plastics molding to speed production by forming more parts per injection process.

Figure 2:
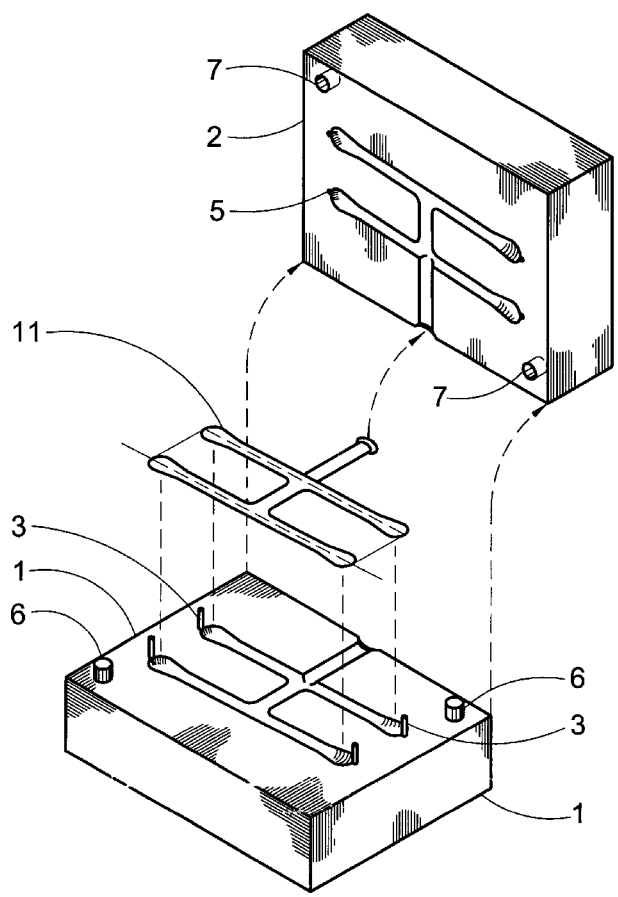

FIG. 2, A view of both mold halves (1, 2) opened after material injection and adequate setting time of a few seconds or more, gives additional perspective into the location of said capturing pins. As mold is closed and prepared for injection, pins (3) perpendicular to the mold face (1), as shown in FIG. 1, are inserted into corresponding receptacle holes (5) in the second mold half (2). Upon fully closing together both mold halves, the halves are held in place by mold pins (6) inserted into corresponding holes (7), a common practice to insure that the halves of the mold do not shift during the injection process. Floss remains clamped in place within shut halves in preparation of injection of material. Clamping pressure flattens floss as it is tightly held between mold halves, and I have found that a slight channel, (not shown) the thickness of the floss at the points the floss lies between mold halves, (not in cavity areas) accommodates the floss. This prevents two problems: possible accidental cutting of floss by mold pressure and escaping injectant from mold cavities (known as flashing) due to floss thickness between mold halves causing inability to confine injectant to mold cavities. Approximate settings used with a single cavity aluminum mold and polypropylene injectant are 475 degrees F., 12 seconds injection time at 60 lbs. clamping pressure for 20 seconds. The resultant product is the flosser (11), shown prior to trimming excess floss and plastic.

Figure 3:
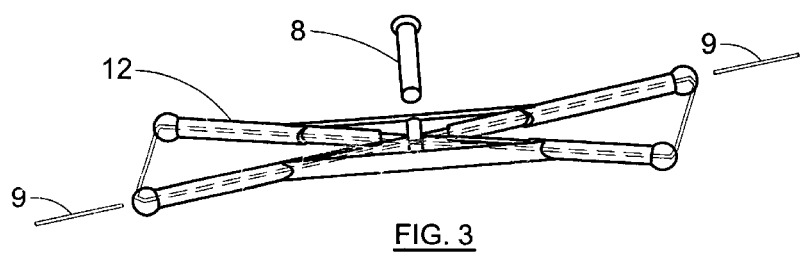

FIG. 3, Shows the completed X-shaped tool (12). Excess plastic (8) and floss (9) are trimmed away. An H-shaped rib for support, smaller but similar in configuration to the tool of FIG. 2, overlies the exact center of the lengthier X-shaped legs of this improved device's design. Floss strand is routed in a figure-eight through the entire length of the frame of the X-shaped device, in the manner of capturing said floss and routing through a plastic injection mold as shown in FIG. 1 and FIG. 2. The tool is then ready to use for flossing teeth by grasping at either of the floss ends between the thumb and forefinger. A leverage action is created in the floss end opposite the grasped end. The working end of the floss may therefore be tensioned to more easily slip between tight contacts and molars as the user inserts floss between teeth, leveraging tension as needed from the grasped end of the tool. The symmetrical tool may be reversed at any time and the second working piece of floss, initially on the side grasped, may then be inserted into the mouth and utilized in the same method as the first to clean interdental contacts and periodontal areas.

If one working length of the floss is worn out or broken, the remaining working length of floss is not effected in any way. Once both working lengths are used up or broken, the worn out part is disposable. Features the X-shaped floss exhibits exclusively are a longer, narrower frame, allowing further reach into mouth with a smaller mouth opening. The fulcrum in center of X retains an H shaped rib for frame reinforcement. Its inherent leverage action is retained as well, and the resultant tool strength is ample. Floss is routed in a figure-eight loop and runs the entire length of the frame in the X-shaped tool, adding to the strength of the tool, in part owed to increased integrity of the floss and plastic combination. Additionally, in the pictured version of the X-shaped tool, leg clearance is provided which allows for fulcrum action in the center of the tool. Squeezing the legs at one flossing end consequently tightens the floss in the opposing set of legs without interference from the tool's geometry of design in its center. It is anticipated that many designs, different materials and cosmetic improvements could afford a similarly constructed tool or device, regardless of the disposability factor of any other device or design. A non-disposable, semi-permanent tool could be built if floss could be made indestructible. Construction costs dictate the tool should be made with the strongest, most durable floss to allow re-use after thorough rinsing.

What is claimed is:

1. A dental flosser framework mold, said mold comprising a substantially planar surface, said surface having a means for capturing and holding a strand of floss, said means comprising a plurality of receptacles formed in said surface in the shape of a flosser framework, and a plurality of pins extending from said surface, said pins and receptacles adapted to securely hold said strand of floss during an injection molding process.

2. A dental flosser comprising a framework having a substantially X-shaped configuration, a strand of floss embedded within and extending throughout substantially the entire framework so that said floss also comprises a substantially X-shaped configuration, said flosser further having an exposed working length of floss at opposing ends of said framework.

* * * * *